United States Patent [19]
Saito et al.

[11] Patent Number: 5,952,337
[45] Date of Patent: Sep. 14, 1999

[54] REMEDY AND PREVENTIVE FOR NERVOUS SYSTEM DISORDERS

[75] Inventors: Ken-Ichi Saito; Tomoko Bessho; Satoshi Yuki; Haruyuki Chaki, all of Kanagawa; Mitsuo Egawa, Tokyo, all of Japan

[73] Assignee: Mitsubishi Chemical Corporation, Tokyo, Japan

[21] Appl. No.: 08/809,544

[22] PCT Filed: Sep. 19, 1995

[86] PCT No.: PCT/JP95/01861

§ 371 Date: May 7, 1997

§ 102(e) Date: May 7, 1997

[87] PCT Pub. No.: WO96/09058

PCT Pub. Date: Mar. 28, 1996

[30] Foreign Application Priority Data

Sep. 21, 1994 [JP] Japan ................................. 6-227085

[51] Int. Cl.[6] ..................................................... A61K 31/44
[52] U.S. Cl. ............................................................. 514/291
[58] Field of Search ............................................. 514/291

[56] References Cited

FOREIGN PATENT DOCUMENTS 0427636  5/1991  European Pat. Off. .
3-218361  9/1991  Japan ....................................... 514/291

*Primary Examiner*—Jerome D. Goldberg
*Attorney, Agent, or Firm*—Sughrue, Mion, Zinn, Macpeak & Seas, PLLC

[57] ABSTRACT

An agent comprising a 4-aminoacyltetrahydrofuro[2,3-b] quinoline derivative represented by formula (I):

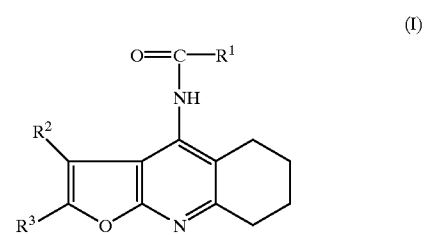

(I)

(wherein $R^1$ represents an alkyl group having 2 to 6 carbon atoms, etc.) or an acid addition salt or a hydrate or a solvent of them as an active ingredient. The compound has a protecting action against neuronal cell death and is useful as a therapeutic or prophylactic agent for cerebrovascular diseases, traumatic head injuries or postencephalitis.

5 Claims, 1 Drawing Sheet

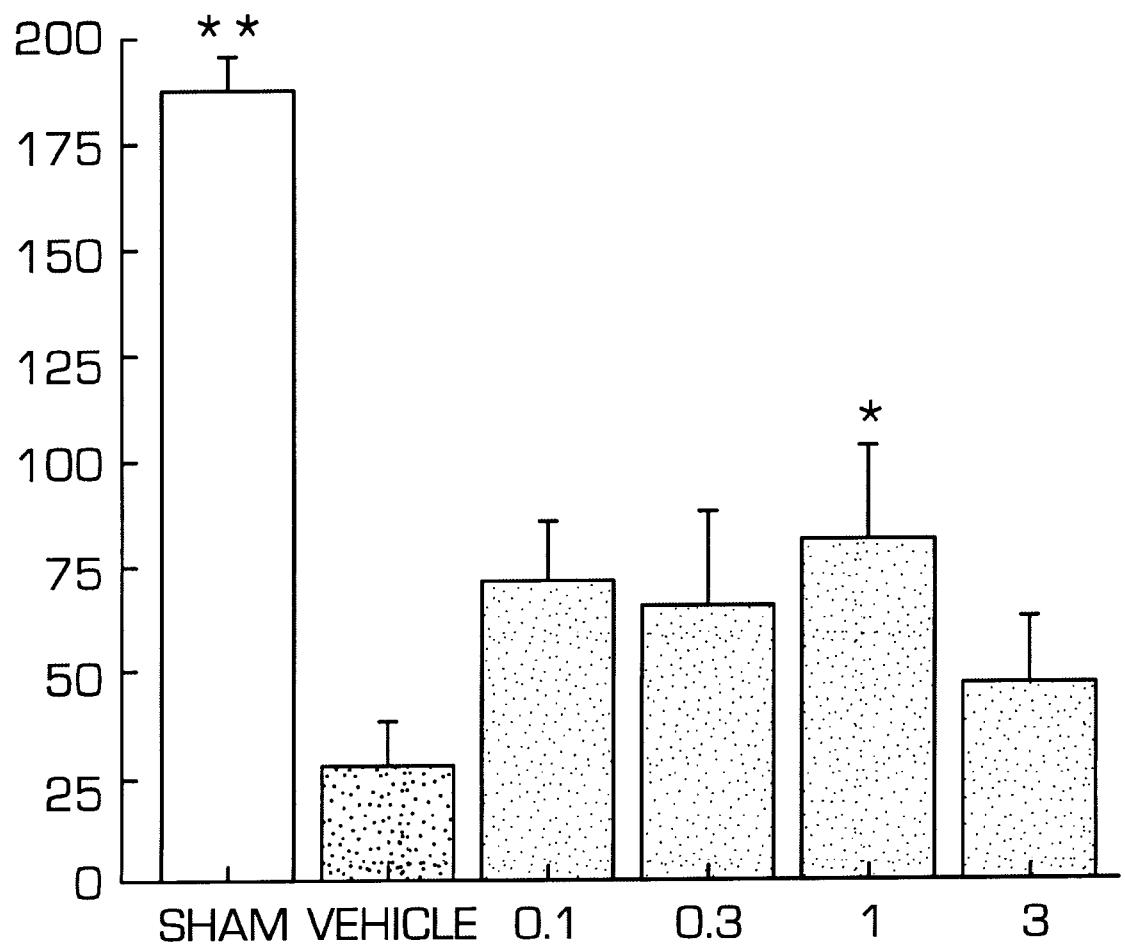
FIGURE

REMEDY AND PREVENTIVE FOR NERVOUS SYSTEM DISORDERS

TECHNICAL FIELD

This invention relates to a therapeutic and prophylactic agent for nervous disturbances comprising a 4-acylaminotetrahydrofuro[2,3-b]quinoline derivative, its acid addition salt, or a hydrate or a solvate thereof as an active ingredient.

BACKGROUND ART

Statistics on causes of death and rates of hospitalization and treatment in the world show that cerebrovascular diseases always rank high. In particular ischemic cerebrovascular diseases are recently increasing as compared with hemorrhagic cerebrovascular diseases. An ischemic cerebrovascular disease is choking of the cerebral blood flow by some causes, ultimately resulting in necrosis of the cerebral tissue. Inter alia, neuronal cells are vulnerable and therefore ready to die on occurrence of ischemia. Neuronal cell death due to ischemia is known to be the most common condition leading to falling off of nerves due to a cerebral disturbance (see *Shinkei Shinpo,* Vol. 36(2), pp. 225–235 (1992) and *Dementia,* Vol. 7, pp. 161–171 (1993). Hence, a substance which prevents neuronal cell death is believed to create a therapeutic and prophylactic agent effective on a cerebrovascular disease. However, such an agent having sufficient efficacy has not yet been found.

It is known that similar neuronal cell death also accompanies a traumatic head injury and postencephalitis (see *J. Neurosurq.,* Vol. 67, pp. 110–119 (1987), *Shinken Shinpo,* Vol. 35(5), pp. 705–716 (1991), and *Taisha,* Vol. 26, pp. 253–257 (1989)). Accordingly, prevention of neuronal cell death is considered to be treatment and prevention effective on these diseases.

It is known that a 4-acylaminotetrahydrofuro[2,3-b] quinoline derivative improves reduced high affinity choline uptake (see JP-A-3-218361, the term "JP-A" as used herein means an "unexamined published Japanese patent application"), but it is unknown that this compound is effective on neuronal cell death.

The inventors of the present invention have extensively studied in order to develop an effective drug on cerebrovascular diseases, traumatic head injuries, postencephalitis, etc. As a result they have found that a 4-acylaminotetrahydrofuro[2,3-b]quinoline derivative and an acid addition salt thereof or a hydrate or a solvate of them have a protecting action against delayed neuronal cell death by cerebral ischemia and completed the present invention.

DISCLOSURE OF THE INVENTION

The gist of the present invention consists in a therapeutic and prophylactic agent for a cerebrovascular disease, a traumatic head injury or postencephalitis which comprises a 4-aminoacyltetrahydrofuro[2,3-b]quinoline derivative represented by formula (I):

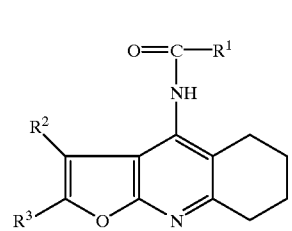

wherein $R^1$ represents an alkyl group having 2 to 6 carbon atoms or a group represented by formula (II) or (III):

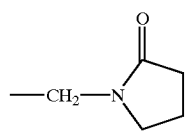

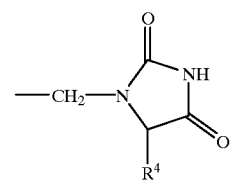

wherein $R^4$ represents a hydrogen atom or an alkyl group having 1 to 6 carbon atoms, and $R^2$ and $R^3$ dependently represent a hydrogen atom or an alkyl group having 1 to 4 carbon atoms, an acid addition salt thereof, or a hydrate or a solvent of them as an active ingredient.

The present invention will be described below in detail.

$R^1$ in the 4-acylaminotetrahydrofuro[2,3-b]quinoline derivative which can be used in the present invention includes an alkyl group having 2 to 6 carbon atoms, preferably an alkyl group having 2 to 4 carbon atoms, such as an ethyl group, an n-propyl group, an isopropyl group, an n-butyl group, a sec-butyl group, or a tert-butyl group. $R^2$ and $R^3$ each include a hydrogen atom and an alkyl group having 1 to 4 carbon atoms, such as a methyl group, an ethyl group, an n-propyl group, an isopropyl group, an n-butyl group, a sec-butyl group, or a tert-butyl group. R4 includes a hydrogen atom and an alkyl group having 1 to 6 carbon atoms. The alkyl group as $R^4$ preferably includes an alkyl group having 1 to 4 carbon atoms, such as a methyl group, an ethyl group, an n-propyl group, an isopropyl group, an n-butyl group, a sec-butyl group, or a tert-butyl group.

The acid in the acid addition salt of the 4-acylaminotetrahydrofuro[2,3-b]quinoline derivative represented by formula (I) includes an inorganic acid, such as hydrochloric acid, hydrobromic acid, hydroiodic acid, sulfuric acid or phosphoric acid; and an organic acid, such as oxalic acid, maleic acid, fumaric acid, lactic acid, malic acid, citric acid, tartaric acid, benzoic acid, methanesulfonic acid, or camphorsulfonic acid. The acid addition salt to be administered should be pharmaceutically acceptable.

The 4-acylaminotetrahydrofuro[2,3-b]quinoline derivative of formula (I) and its acid addition salt may exist in the form of a hydrate or a solvate, which is also included in the compounds according to the present invention.

The process for preparing the 4-acylaminotetrahydrofuro [2,3-b]quinoline derivative of formula (I) and the like is not particularly limited. For example, the compound of the invention can easily be synthesized according to the process described in JP-A-3-218361.

The 4-acylaminotetrahydrofuro[2,3-b]quinoline derivative of formula (I) and the like possess a protecting action against delayed neuronal cell death by cerebral ischemia as demonstrated in Examples hereinafter given. The 4-acylaminotetrahydrofuro[2,3-b]quinoline derivative of formula (I) and the like having such an action can be used as a therapeutic and prophylactic agent for a cerebrovascular disease, a traumatic head injury or postencephalitis, preferably a therapeutic and prophylactic agent against dementia, reduction of power of concentration, lalopathy, reduction of volition, emotional disorders, hallucination and/or delusion, and behavioral disorders that are manifestations of cerebrovascular diseases, traumatic head injuries, postencephalitis, etc.

In using the 4-acylaminotetrahydrofuro[2,3-b]quinoline derivative of formula (I) and the like as a therapeutic or prophylactic agent, they are administered either alone or as bound to a pharmaceutically acceptable carrier. The composition of the agent is decided by the solubility and chemical properties of the compound, the administration route, the administration schedule, and the like. For example, the compound can be administered orally in the form of granules, powders, pulvules, tablets, hard capsules, soft capsules, syrups, emulsions, suspensions, solutions, etc. or injected intravenously, intramuscularly or subcutaneously in the form of an injectable solution.

The compound made up in powder for injection can be made into an injectable solution on use. An organic or inorganic carrier (solid or liquid) or diluent for medical use which is suitable for oral, rectal, non-oral or topical administration can be used together with the 4-acylaminotetrahydrofuro[2,3-b]quinoline derivative of formula (I) and the like. Vehicles used in the preparation of solid preparations include lactose, sucrose, starch, talc, cellulose, dextrin, kaolin, and calcium carbonate. Liquid preparations for oral administration, i.e., emulsions, syrups, suspensions, solutions, etc., contain commonly employed inert diluents, such as water and vegetable oil. These preparations can contain adjuvants, such as wetting agents, suspending assistants, sweeteners, aromatics, colorants or preservatives, in addition to the inert diluents. A liquid preparation may be encapsulated into capsules made of an absorbable substance, such as gelatin. Solvents or suspending agents used in the preparation of non-oral dose forms, such as an injectable solution, include water, propylene glycol, polyethylene glycol, benzyl alcohol, ethyl oleate, and lecithin. The preparations can be made up in a conventional manner.

The clinical dosage generally ranges from 1 to 2000 mg, preferably from 1 to 500 mg, per day for an adult in oral administration. It is preferably adjusted appropriately depending on the age of the patient, the symptoms and conditions of the disease, and whether any other drug is concurrently administered. A daily dose may be given in a single dose or 2 or 3 divided doses at an appropriate interval or intermittently. A dose for injection ranges from 0.1 to 100 mg, preferably 0.1 to 50 mg, a day for an adult.

BRIEF DESCRIPTION OF DRAWINGS

The Figure is a graph showing the action of 2-(2-oxopyrrolidin-1-yl)-N-(2,3-dimethyl-5,6,7,8-tetrahydrofuro[2,3-b]quinolin-4-yl)acetamide on delayed neuronal cell death in rats, in which the abscissa indicates groups on the drug (dose: 0.1, 0.3, 1, or 3 mg/kg), and the ordinate the number of cells per mm.

THE BEST MODE FOR CARRYING OUT THE INVENTION

The present invention will now be illustrated in greater detail with reference to Examples, but it should be understood that the present invention is not construed as being limited thereto without departing from the scope thereof.

2-(2-Oxopyrrolidin-1-yl)-N-(2,3-dimethyl-5,6,7,8-tetrahydrofuro[2,3-b]quinolin-4-yl)acetamide, which is the 4-acylaminotetrahydrofuro[2,3-b]quinoline derivative of formula (I), was synthesized in accordance with the process described in JP-A-3-218361 for use in the following experiments.

EXAMPLE 1

Action on Delayed Nerve Cell Death in Rat

Bilateral vertebral arteries of Wistar male rats weighing 250 to 270 g were electrically cauterized one day before ischemia induction to prepare rats showing no nervous involvement such as hemiplegia.

One hour before ischemia induction, 0.1, 0.3, 1, or 3 mg/kg-b.w. of 2-(2-oxopyrrolidin-1-yl)-N-(2,3-dimethyl-5,6,7,8-tetrahydrofuro[2,3-b]quinolin-4-yl)acetamide suspended in a 0.5% Tween solution or physiological saline containing an equivalent amount of a vehicle was orally given to the rat. Ischemia was inducted by 10-minutes' bilateral occlusion of the common carotid arteries. Those rats who did not show disappearance of righting reflex during the occlusion were excluded. During the experiment, care was taken to maintain the body temperature of the rats. After 72 hours from the recirculation, the brain of the rat under pentobarbital anesthesia was fixed by perfusion with a fixative, FAM (formalin:acetic acid:methanol=1:1:8) through the heart. A 5 $\mu$m thick slice of the forebrain was prepared in a usual manner, and the Nissl bodies were stained. The number of hippocampus CA1 pyramidal cells were counted to obtain the number of the cells per mm (neuronal density).

The results obtained are shown in the Figure 2-(2-Oxopyrrolidin-1-yl)-N-(2,3-dimethyl-5,6,7,8-tetrahydrofuro[2,3-b]quinolin-4-yl)acetamide showed a tendency of suppressing delayed neuronal cell death in a dose of 0.1 to 1 mg/kg. The "Sham" in the Figure is a group which underwent bilateral cauterization of vertebral arteries but had no ischemia. P of the Sham group was less than 0.01, and that of the 1 mg/kg group was less than 0.05.

Industrial Applicability

The 4-acylaminotetrahydrofuro[2,3-b]quinoline derivative according to the present invention has a protecting action against neuronal cell death and is useful as a therapeutic and prophylactic agent for a cerebrovascular disease, a traumatic head injury, postencephalitis, etc.

We claim:

1. A method for treating and preventing cerebrovascular disease, traumatic head injury or postencephalitis comprising administering to a subject in need of treatment an effective amount of a 4-aminoacyltetrahydrofuro[2,3-b] quinoline derivative represented by formula (I):

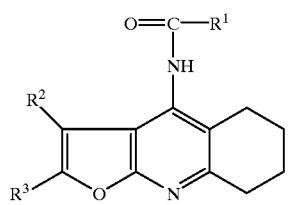

(I)

wherein R¹ represents an alkyl group having 2 to 6 carbon atoms or a group represented by formula (II) or (III):

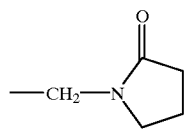

(II)

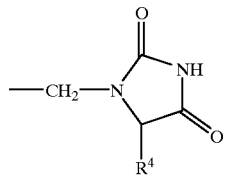

(III)

wherein $R^4$ represents a hydrogen atom or an alkyl group having 1 to 6 carbon atoms, and $R^2$ and $R^3$ independently represent a hydrogen atom or an alkyl group having 1 to 4 carbon atoms, an acid addition salt thereof, a hydrate thereof, or a solvent thereof as an active ingredient, and a pharmaceutically acceptable carrier.

2. The method for treating and preventing cerebrovascular disease as claimed in claim 1, wherein said 4-aminoacyltetrahydrofuro[2,3-b]quinoline derivative is orally administered in an amount of from 1 to 2000 mg/day.

3. The method for treating and preventing cerebrovascular disease as claimed in claim 1 wherein said 4-aminoacyltetrahydrofuro[2,3-b]quinoline derivative is orally administered in an amount of from 1 to 500 mg/day.

4. The method for treating and preventing cerebrovascular disease as claimed in claim 1, wherein said 4-aminoacyltetrahydrofuro[2,3-b]quinoline derivative is administered by injection in an amount of from .1 to 100 mg/day.

5. The method for treating and preventing cerebrovascular disease as claimed in claim 1, wherein said 4-aminoacyltetrahydrofuro[2,3-b]quinoline derivative is administered by injection in an amount of from .1 to 50 mg/day.

* * * * *